(12) United States Patent
Kumar

(10) Patent No.: US 8,024,037 B2
(45) Date of Patent: Sep. 20, 2011

(54) EXTERNAL DEFIBRILLATOR

(76) Inventor: Uday N. Kumar, San Francisco, CA (US)

(*) Notice: Subject to any disclaimer, the term of this patent is extended or adjusted under 35 U.S.C. 154(b) by 465 days.

(21) Appl. No.: 11/829,753

(22) Filed: Jul. 27, 2007

(65) Prior Publication Data

US 2008/0033495 A1 Feb. 7, 2008

Related U.S. Application Data

(60) Provisional application No. 60/834,556, filed on Aug. 1, 2006.

(51) Int. Cl.
*A61N 1/39* (2006.01)
(52) U.S. Cl. .......................................................... 607/5
(58) Field of Classification Search .................. 600/507; 607/4–8
See application file for complete search history.

(56) References Cited

U.S. PATENT DOCUMENTS

| | | | |
|---|---|---|---|
| 4,928,690 A * | 5/1990 | Heilman et al. .................. 607/4 |
| 5,078,134 A | 1/1992 | Heilman et al. | |
| 5,741,306 A | 4/1998 | Glegyak et al. | |
| 5,803,927 A * | 9/1998 | Cameron et al. .................. 607/5 |
| 5,929,601 A | 7/1999 | Kaib et al. | |
| 5,944,669 A | 8/1999 | Kaib | |
| 6,065,154 A | 5/2000 | Hulings et al. | |
| 6,097,982 A | 8/2000 | Glegyak et al. | |
| 6,169,387 B1 | 1/2001 | Kaib | |
| 6,253,099 B1 | 6/2001 | Oskin et al. | |
| 6,280,461 B1 | 8/2001 | Glegyak et al. | |
| 6,678,559 B1 * | 1/2004 | Breyen et al. .................. 607/5 |
| 6,681,003 B2 | 1/2004 | Linder et al. | |
| 2003/0004547 A1 * | 1/2003 | Owen et al. .................. 607/5 |
| 2003/0095648 A1 | 5/2003 | Kaib et al. | |
| 2006/0259091 A1 * | 11/2006 | Ries et al. .................. 607/36 |

* cited by examiner

*Primary Examiner* — Eric D. Bertram
(74) *Attorney, Agent, or Firm* — Shay Glenn LLP

(57) ABSTRACT

An external defibrillator having a battery; a capacitor electrically communicable with the battery; at least two electrodes electrically communicable with the capacitor and with the skin of a patient; a controller configured to charge the capacitor from the battery and to discharge the capacitor through the electrodes; and a support supporting the battery, capacitor, electrodes and controller in a deployment configuration, the defibrillator having a maximum weight per unit area in the deployment configuration of 0.1 lb/in$^2$ and/or a maximum thickness of 1 inch. The support may be a waterproof housing.

6 Claims, 6 Drawing Sheets

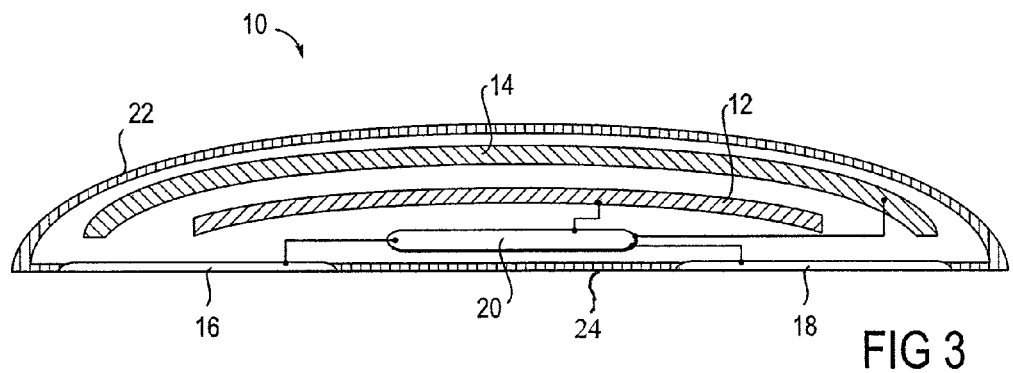
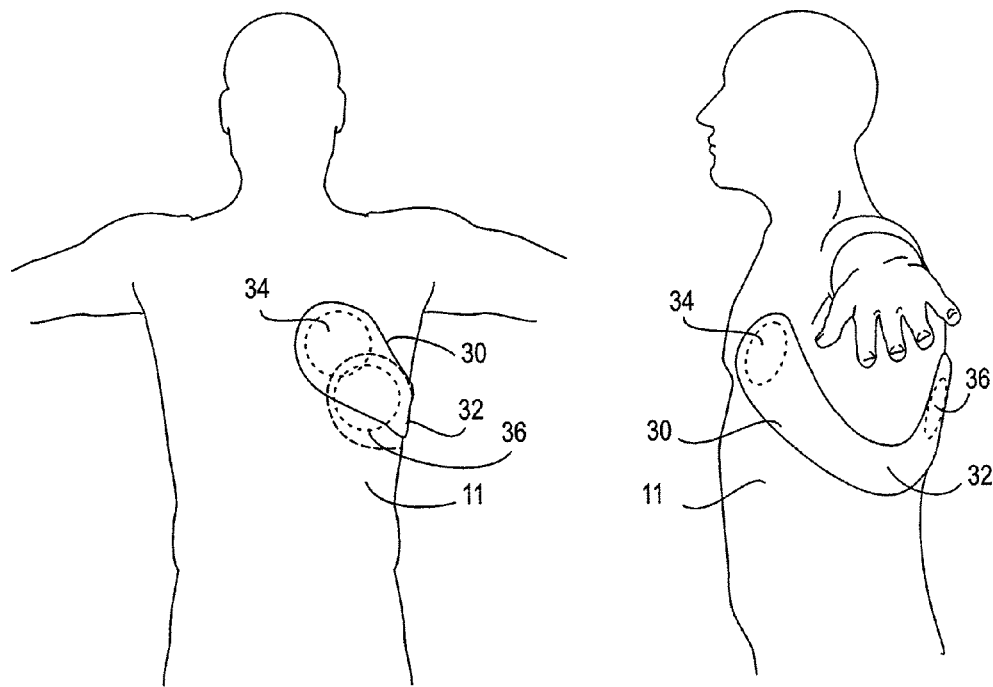
FIG 3
FIG 4
FIG 5

EXTERNAL DEFIBRILLATOR

CROSS REFERENCE TO RELATED APPLICATIONS

This application claims priority under 35 U.S.C. §119 to U.S. Provisional Patent Application No. 60/834,556, filed Aug. 1, 2006, and entitled "Non-Invasively Affixed Device for Cardiac Defibrillation," which is incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

The present invention relates generally to external defibrillators. In particular, the invention relates to automatic external defibrillators that can be continuously and easily worn by a patient for an extended period of time.

Every year in the US, over 800,000 individuals have a heart attack, or myocardial infarction (MI). After an MI, a patient is at increased risk for experiencing potentially life-threatening abnormal heart rhythms, or arrhythmias. This increased risk is caused by numerous structural and electrical abnormalities in the recently damaged heart. For most patients, however, this increased risk is temporary. After patients have been treated with various procedures and medications to help their heart heal, their risk of experiencing a life-threatening arrhythmia usually drops back to their risk prior to the MI. This drop in risk typically occurs after a few days to weeks after the MI has taken place.

Various studies of this population of patients have shown that certain medications, especially those with anti-arrhythmic properties, do a poor job at reducing this temporarily increased arrhythmia risk. Additionally, implantable cardioverter defibrillators (ICDs), which are devices that can effectively reset the heart rhythm when an arrhythmia occurs, carry significant risks during implantation such that their overall benefit during this short period of increased risk is limited. Implanting ICDs in many patients whose risk of an arrhythmia would eventually return to normal also has significant unwanted health, economic, and societal consequences.

Automatic external defibrillators (AEDs), which can be very effective in highly populated places such as airports, are only useful if other people capable of using the AED are present at the time an arrhythmia occurs and can identify that a patient needs defibrillation; this may often not be the case for most people living at home. Finally, current methods of temporary defibrillation, such as wearable defibrillator vests, are not routinely used due to difficulty for patients to comply with such systems because of the obtrusiveness of the device, the inability to use such systems when wet, etc. Wearable external defibrillators and external cardioverter defibrillators are described in U.S. Pat. No. 5,741,306; U.S. Pat. No. 6,065,154; U.S. Pat. No. 6,280,461; U.S. Pat. No. 6,681,003 and US 2003/0095648, and a similar product is currently being sold as the Zoll Lifecor LifeVest™ wearable cardioverter defibrillator. Due to all of these limitations, the vast majority of patients are sent home after an MI without any type of temporary protection from a potentially life-threatening arrhythmia.

In addition to the post-MI setting, there are other situations in which a patient's arrhythmia risk is temporarily increased, such as after certain types of heart surgery or when starting certain medications with pro-arrhythmic properties. In patients who are known to be at risk for an arrhythmia and who have an ICD in place, if the ICD needs to be removed for a short period of time due to an infection or malfunction, the patient is also left vulnerable. In other patients, such as those with a condition known as heart failure, certain medications and/or procedures can lead to an improvement in the heart's function and reduce a patient's susceptibility to an arrhythmia such that a permanently implanted device, such as an ICD, would not be needed. However, during the time of treatment when heart function is recovering, these patients are still temporarily at risk for a life-threatening arrhythmia.

SUMMARY OF THE INVENTION

One drawback of currently available wearable defibrillators (such as the LifeVest product) is lack of patient compliance. Because of the size, shape and weight of these wearable devices, patients are reluctant to wear them due to discomfort, their bulkiness under clothes or limitations in the devices themselves. In particular, such devices cannot be worn in the shower or bath, and they often are difficult, if not impossible, to sleep in. What is needed, therefore, is a non-invasive, temporary device that can monitor the patient's heart rhythm to detect arrhythmias; can automatically and reliably defibrillate the heart if an arrhythmia is detected; can be used for a short period of time (days to weeks, possibly months) when the temporary risk of an arrhythmia exists; is entirely non-invasive and reversible and causes no significant or potentially permanent bodily harm from its use; and/or, most importantly, is unobtrusive and waterproof and requires only minimal maintenance or care so that it can seamlessly integrate into patients' lives such that they are protected from life-threatening arrhythmias during this entire period of time. If the device is required to defibrillate a patient during this time, this patient can then be referred for implantation of a permanent ICD, if appropriate. If nothing occurs and the patient doesn't have persistent pro-arrhythmic risk factors after this temporary period, the device can be removed and the implantation of a permanent device can be avoided. In this way, a functional, easy-to-use device for cardiac defibrillation to protect patients during a period of temporarily increased arrhythmia risk could also more efficiently identify patients who would benefit from more permanently implanted devices and those who would not.

One aspect of the invention provides an external defibrillator having a battery; a capacitor electrically communicable with the battery; at least two electrodes electrically communicable with the capacitor and with the skin of a patient; a controller configured to charge the capacitor from the battery and to discharge the capacitor through the electrodes; and a support supporting the battery, capacitor, electrodes and controller in a deployment configuration, the defibrillator having a maximum weight per unit area in the deployment configuration of 0.1 lb/in$^2$.

In some embodiments, the capacitor has a capacitance of at least 25 microFarads. In some embodiments, the electrodes are spaced at least 3 inches apart. In some embodiments, the defibrillator has a maximum thickness of 1 inch.

In some embodiments the external defibrillator also has an electrocardiogram (ECG) monitor, the controller being further configured to charge the capacitor from the battery and to discharge the capacitor through the electrodes in response to an arrhythmia detected by the ECG monitor.

In some embodiments, the support is conformable to a human torso. The support may also have adhesive adapted to attach the defibrillator to human skin. In some embodiments, the support may include a waterproof housing for the battery, the capacitor, the electrodes and the controller.

Another aspect of the invention provides an external defibrillator having a battery; a capacitor electrically communicable with the battery; at least two electrodes electrically communicable with the capacitor; a controller configured to charge the capacitor from the battery and to discharge the capacitor through the electrodes; and a support supporting the battery, capacitor, electrodes and controller in a deployment configuration, the defibrillator having a maximum thickness of 1 inch.

In some embodiments, the capacitor has a capacitance of at least 25 microFarads. In some embodiments, the electrodes are spaced at least 3 inches apart. Some embodiments according to this aspect of the invention also include an ECG monitor, the controller being further configured to charge the capacitor from the battery and to discharge the capacitor through the electrodes in response to an arrhythmia detected by the ECG monitor.

In some embodiments, the support is conformable to a human torso. The support may also include adhesive adapted to attach the defibrillator to human skin and/or a waterproof housing for the battery, the capacitor, the electrodes and the controller.

Yet another aspect of the invention provides a method of treating heart arrhythmias in a patient including the following steps: engaging an external defibrillator with the patient, the engaging step including the step of attaching a support to the patient, the support supporting a battery, a capacitor, a controller, an ECG monitor and two electrodes; placing the two electrodes in electrical contact with the patient's skin; leaving the support attached to the patient and the electrodes in electrical contact with the patient's skin for at least 30 days; and monitoring the patient's ECG with the ECG monitor while the electrodes are in contact with the patient's skin. In some embodiments, the method includes the step of delivering a shock to the patient in response to a monitored arrhythmia.

In some embodiments, the engaging step includes the step of providing a waterproof housing for the battery, the capacitor, the controller and the ECG monitor. In some embodiments, the engaging step includes the step of supporting the defibrillator on the patient so that the battery, the capacitor, the controller, the ECG monitor and the electrodes have a maximum weight per unit area of 0.1 lb/in$^2$. In some embodiments, the engaging step includes the step of supporting the defibrillator on the patient so that the battery, the capacitor, the controller, the ECG monitor and the electrodes have a maximum thickness of 1 inch.

In some embodiments, the engaging step includes the step of conforming the support to the patient's torso. In some embodiments, the attaching step includes the step of attaching the support to the patient's skin with adhesive.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3 is a cross-sectional view of the external defibrillator of FIGS. 1 and 2.

FIG. 4 shows a external defibrillator according to another embodiment of the invention in place on a patient.

FIG. 5 is a side view of the embodiment of FIG. 4 in place on a patient.

DETAILED DESCRIPTION OF THE INVENTION

Figure 1:
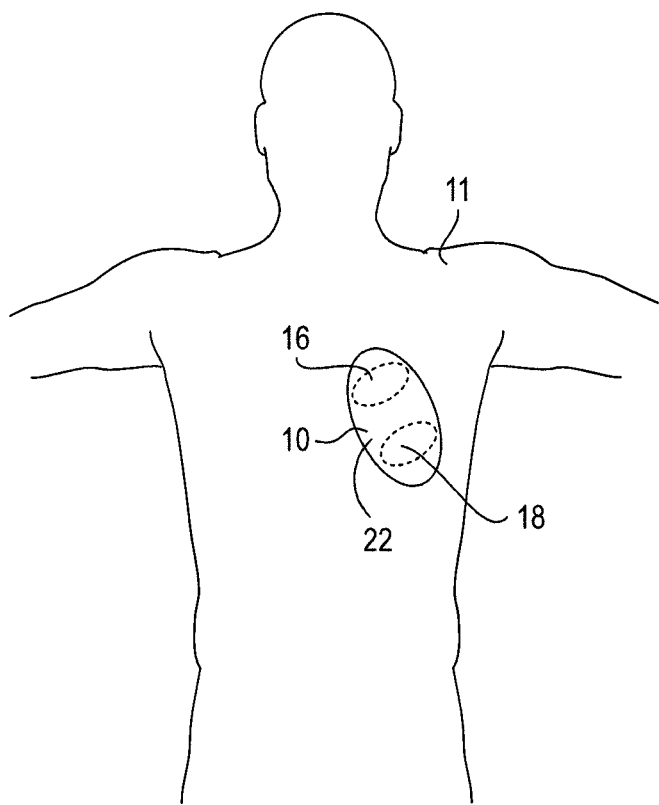
FIG. 1 shows a external defibrillator according to one embodiment of the invention in place on a patient.
Figure 2:
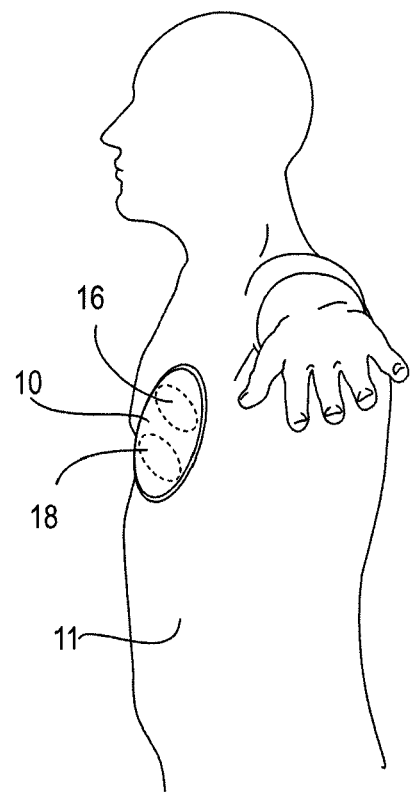
FIG. 2 is a side view of the embodiment of FIG. 1 in place on a patient.

FIGS. 1-3 show one embodiment of the external defibrillator of this invention. (For purposes of this application, the terms "defibrillator" and "external defibrillator" include external cardioverters and cardioverter defibrillators as well.) As shown in FIGS. 1 and 2, defibrillator 10 has been engaged with a patient 11 by attaching to the front of the patient's torso. In this embodiment, defibrillator 10 has a battery 12, a capacitor 14, a pair of electrodes 16 and 18, and a controller 20. Capacitor 14 may have a capacitance between 25 and 300 micro Farads. Electrodes 16 and 18 are preferably at least 3 inches apart in order to place them in the proper orientation for use on an adult. In some embodiments, more than two electrodes may be used. A support 22 supports the battery, capacitor, electrodes and controller. In this embodiment, support 22 is a waterproof housing. Adhesive 24 on the electrode side of the defibrillator may be used to attach the defibrillator to the patient.

Defibrillator 10 has a design that distributes the weight of its components in order to make the device more comfortable to wear. In one embodiment, for example, the components are designed and distributed so that the defibrillator has a maximum weight per unit area of 0.1 lb/in$^2$. In addition, battery 12 and capacitor 14 have shapes that help conform the device to the shape of the patient's torso.

In addition, in order to make the device easily worn beneath clothes, defibrillator 10 has a maximum thickness of 1 inch. In addition, in one embodiment, support housing 22 is conformable to the patient's torso in order to improve the comfort and reduce the bulkiness of the device. In this embodiment, integration of the main components of the defibrillator into a single housing helps achieve the desired size and weight distribution parameters.

To engage the defibrillator 10 to the patient, the adhesive 24 is applied to the patient's bare chest in order to hold electrodes 16 and 18 (including any electrode gel or other material) in place on the patient's skin. Once in place, the patient may wear ordinary clothes over the device and may go about normal daily activities. Of particular importance is the waterproof nature of this embodiment, enabling the patient to continue to wear the defibrillator continuously, even in the shower or bath. The patient may continue to wear the device as long as necessary, such as up to 30 continuous days, until the patient is no longer at risk for cardiac arrhythmias or until an ICD can be implanted, if necessary.

While it is in place on the patient, an ECG monitor that is part of controller 20 monitors the patient's ECG through electrodes 16 and 18. If the ECG monitor detects an arrhythmia requiring a shock, controller 20 will draw current from battery 12 to charge capacitor 14. When capacitor 14 has been charge to an appropriate voltage, controller 20 will then disengage the ECG monitor and cause capacitor 14 to discharge across electrodes 16 and 18 in, e.g., a truncated biphasic waveform or other suitable waveform. The ECG monitor will then re-engage to determine if the shock successfully converted the patient's arrhythmia to a safer rhythm. If the patient is still in a shockable rhythm, the charge and shock sequence will repeat until the patient's rhythm is converted to a safer rhythm. Additional sensors (such as accelerometers, skin impedance sensors, blood oxygen saturation sensors, etc.) may be used in addition to the ECG monitor to detect the need for a shock. Defibrillator 10 may also provide an optional audible and/or visual warning of the need for a shock or of an impending shock through a speaker and/or display (not shown). Defibrillator 10 may also have an override switch (not shown) for use by the patient or bystander to override the charge and shock sequence.

Alternative external defibrillator designs are shown in FIGS. 4-7. In FIGS. 4 and 5, the defibrillator 30 is supported by a support 32 that places electrodes 34 and 36 on either side of the patient's torso. Support 32 may be a waterproof housing containing all (or substantially all) defibrillator components that is conformable to the patient's torso and attached to the patient's skin with adhesive. As in earlier embodiments, the components are designed and distributed so that the defibrillator has a maximum weight per of 0.1 lb/in$^2$. In addition, in order to make the device easily worn beneath clothes, defibrillator 30 has a maximum thickness of 1 inch.

Figure 6:
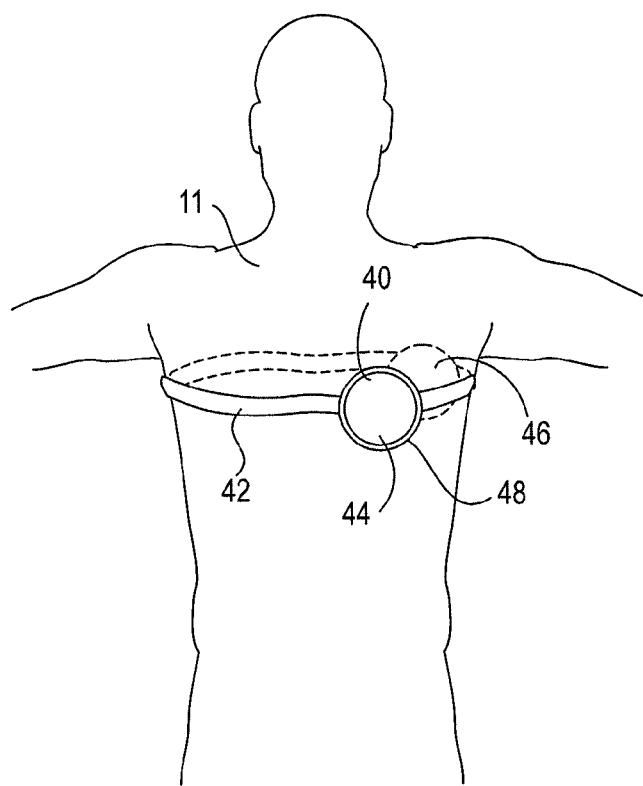
FIG. 6 shows a external defibrillator according to yet another embodiment of the invention in place on a patient.
Figure 7:
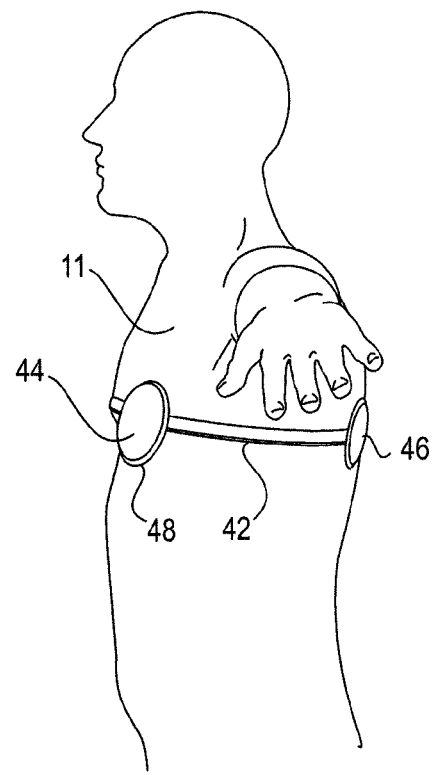
FIG. 7 is a side view of the embodiment of FIG. 6 in place on a patient.

In FIGS. 6 and 7, the defibrillator 40 is supported by a strap support 42 that circumscribes the patient's torso and places electrodes 44 ands 46 on either side of the patient's torso. In this embodiment, the defibrillator's battery, capacitor and control circuitry are within a housing 48 supporting electrode 44. Wires communicating electrode 46 with the remaining defibrillator components pass through or adjacent strap support 42. In some embodiments, each of the distributed components (with the exception of the strap support 42) has a maximum weight per unit area of 0.1 lb/in$^2$.

Figure 8A:
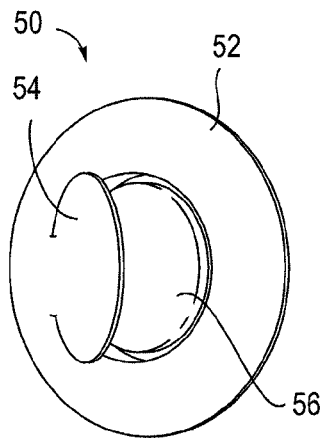
FIGS. 8A-C show an embodiment of the invention with a replaceable battery.
Figure 8B:
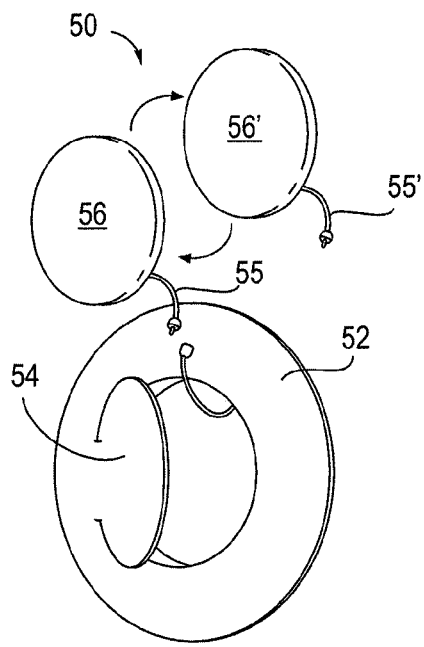
Figure 8C:
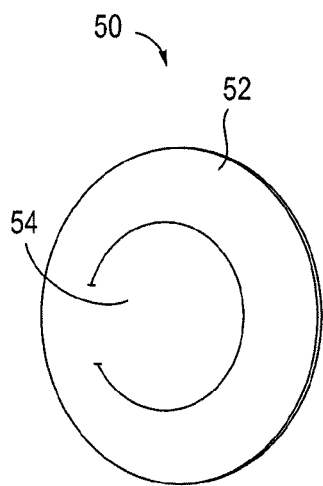

FIGS. 8A-C show an embodiment of a external defibrillator in which the battery is easily replaced. The components of external defibrillator 50 are supported by a housing 52. A door 54 may be opened in housing 52 to provide access to a removable battery 56, which is disconnected from the rest of the defibrillator by disconnecting its connector 55. A replacement battery 56' may be put into housing 52 through door 54, as shown in FIG. 8B, connected to the other defibrillator components via connector 55', and the door 54 may then be closed, as shown in FIG. 8C. These steps may all be performed while housing 52 is attached to the patient, such as by adhesive, glue, straps, etc.

In alternative embodiments, the battery can be recharged.

Figure 9A:
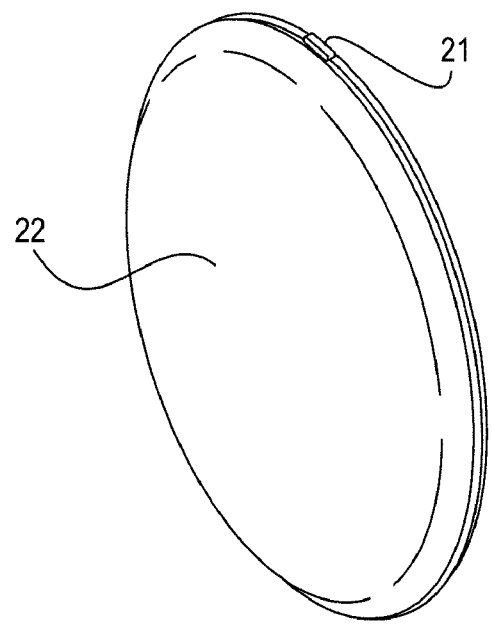
FIGS. 9A-B show an embodiment of the invention with a replaceable housing.
Figure 9B:
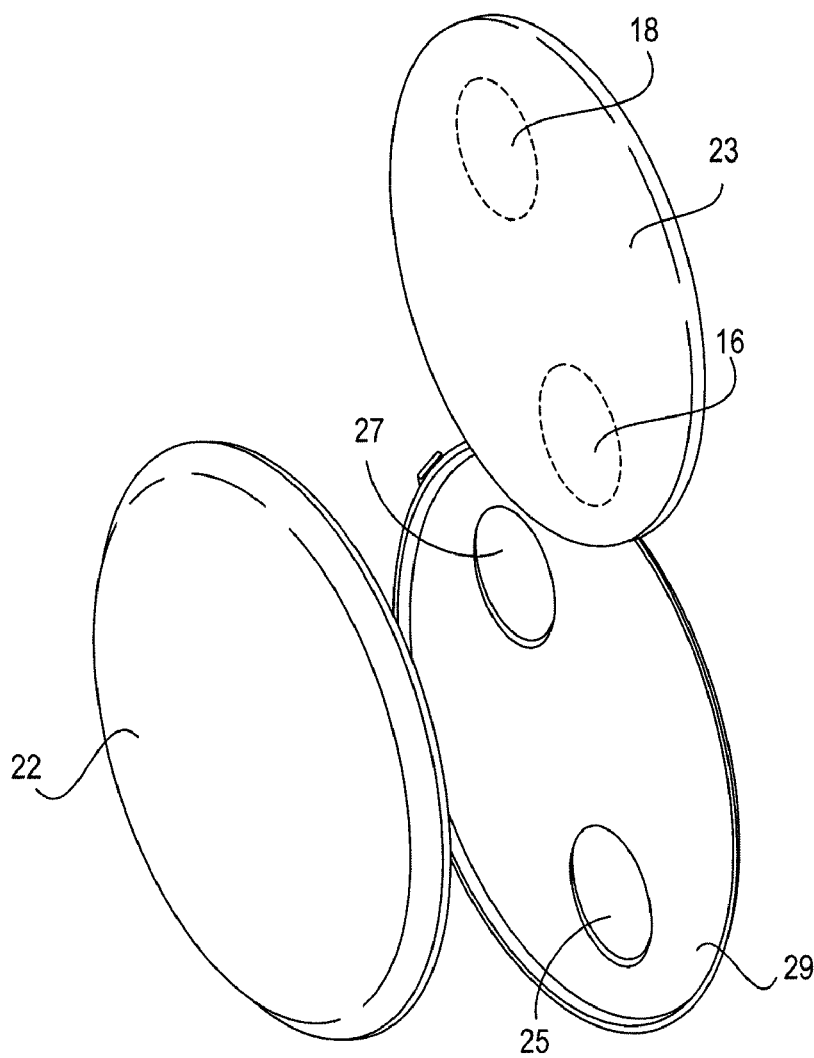

When the external defibrillator is no longer needed by the patient, it may be removed. If the defibrillator support has been attached by adhesive or glue, or if the support was damaged or soiled, it may be necessary to provide a new housing for the defibrillator components. With respect to the embodiment of FIGS. 1-3, for example, the housing 22 may be opened (by operating a latch, zipper or other opener 21) and the defibrillator components (shown together as element 23, with electrodes 16 and 18 shown in phantom) may be removed from the housing, as shown in FIGS. 9A-B. The bottom portion 29 of housing 22 has two openings 25 and 27 which line up with electrodes 16 and 18 when the defibrillator is disposed in the housing. These defibrillator components may then be placed in a new housing for use on a new patient or on the same patient, and the old housing may be discarded.

Figure 10A:
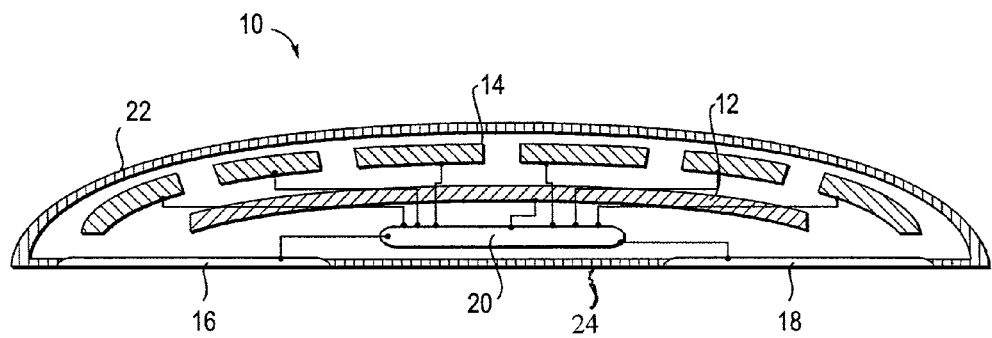
FIG. 10A shows an external defibrillator with an alternative capacitor configuration.

The capacitor used in external defibrillators of this invention may be long and wide with a narrow spacing to provide the required capacitance. Alternatively, the capacitor 14 may be formed as multiple capacitors connected in parallel, as shown in FIG. 10A, to provide the required capacitance.

Figure 10B:
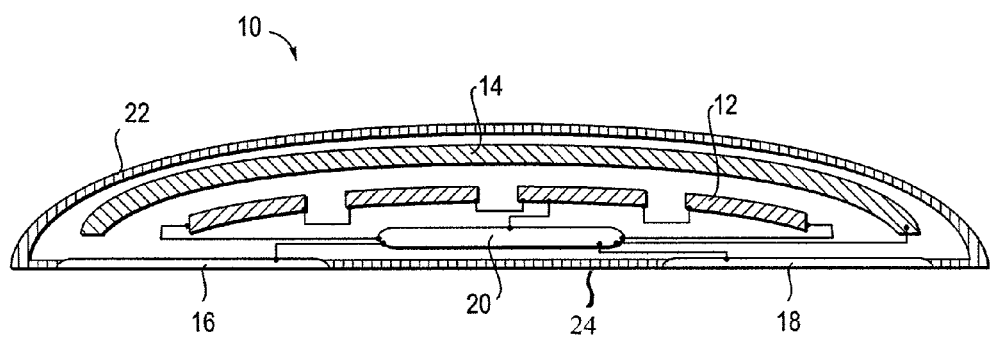
FIG. 10B shows an external defibrillator with an alternative battery configuration.

Likewise, the battery used in external defibrillators of this invention can be made thin and with a relatively large surface area. For example, battery 12 may be formed as multiple batteries connected in series to provide the required current and voltage to charge the capacitor, as shown in FIG. 10B. Any suitable battery technology may be used, such as combinations of pastes of powdered chemicals, liquid electrolytes and metal plates. The defibrillator housing may also serve as the battery casing.

What is claimed is:

1. A unitary external defibrillator comprising:
   a battery;
   a capacitor electrically communicable with the battery;
   at least two electrodes electrically communicable with the capacitor and with the skin of a patient;
   a controller configured to charge the capacitor from the battery and to discharge the capacitor through the electrodes;
   a housing supporting the battery, capacitor, electrodes and controller in a deployment configuration and at least partially surrounding all defibrillator components to create a unitary defibrillator with a maximum weight per unit area in the deployment configuration of 0.1 lb/in$^2$ and a maximum thickness of 1 inch; and
   adhesive adapted to attach the unitary defibrillator to human skin in the deployment configuration.

2. The unitary external defibrillator of claim 1 wherein the capacitor has a capacitance of at least 25 microFarads.

3. The unitary external defibrillator of claim 1 wherein the electrodes are spaced at least 3 inches apart.

4. The unitary external defibrillator of claim 1 further comprising an ECG monitor, the controller being further configured to charge the capacitor from the battery and to discharge the capacitor through the electrodes in response to an arrhythmia detected by the ECG monitor.

5. The unitary external defibrillator of claim 1 wherein the housing is conformable to a human torso.

6. The unitary external defibrillator of claim 1 wherein the housing is waterproof.

* * * * *